US00PP23019P3

(12) United States Plant Patent
Korlipara

(10) Patent No.: US PP23,019 P3
(45) Date of Patent: Sep. 4, 2012

(54) *ECHINACEA* PLANT NAMED 'AMAZING DREAM'

(50) Latin Name: ***Echinacea* spp.**
Varietal Denomination: Amazing Dream

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 81 days.

(21) Appl. No.: 12/931,221

(22) Filed: Jan. 26, 2011

(65) Prior Publication Data

US 2012/0192323 P1 Jul. 26, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu

(74) *Attorney, Agent, or Firm* — Klarquist Sparkman, LLP

(57) ABSTRACT

A new and distinct *Echinacea* plant named 'Amazing Dream' characterized by an amazing number of inflorescences starting in the first season, a very long bloom time with excellent rebloom, a very compact habit, deep pink ray florets surrounding dark cones, numerous, strong stems, and excellent vigor.

1 Drawing Sheet

Botanical denomination: *Echinacea* spp.

Variety designation: 'Amazing Dream'.

The present invention relates to a new and distinct cultivar of *Echinacea* and given the cultivar name 'Amazing Dream'. *Echinacea* is in the family Asteraceae. This new cultivar is a third generation seeding originating from a planned breeding program using *Echinacea tennesseensis* in the original cross. The exact parents are unknown, unnamed, proprietary plants. The program goal was for the compact habits and strong stems of *Echinacea tennesseensis* on garden worthy plants with long lasting, saturated flower colors. The new cultivar is the first in this group to be introduced.

Compared to *Echinacea* 'CBG Cone 2', also known as Pixie Meadowbrite™ (U.S. Plant Pat. No. 18,546), the new cultivar is much more compact.

Compared to *Echinacea* 'Kim's Knee High' (U.S. Plant Pat. No. 12,242), the new cultivar has larger inflorescences and its ray florets are more horizontal.

Compared to *Echinacea* 'Raspberry Tart' (U.S. Plant Pat. No.18,933), the new cultivar has ray florets that are less intensely pink and held more upright, more basal crowns, and is much longer blooming.

This new *Echinacea* cultivar is uniquely distinguished by:

1. an amazing number of inflorescences starting in the first season,
2. very long bloom time with excellent rebloom,
3. very compact habit,
4. deep pink ray florets surrounding dark cones,
5. numerous, strong stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows the inflorescences and habit of *Echinacea* 'Amazing Dream' as a nine-month-old growing in the field in full sun in early July in Canby, Oreg.

DETAILED PLANT DESCRIPTION

The following is a detailed description of the new *Echinacea* cultivar based on observations of 18-month-old specimens growing in the 2-gallon pots in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type.*—Herbaceous perennial.

*Hardiness.*—USDA Zones 4 to 9.

*Size.*—Grows to about 46 cm wide and 45 cm tall to top of inflorescences.

*Form.*—Basal clump, with about 50 stems from the base.

*Vigor.*—Excellent.

*Roots.*—Fibrous, with many downward growing and few laterals, ivory in color, Yellow White 158D, roots develop easily from cuttings from the crown.

Stem (flowering):

*Type.*—Ascending, with 1 (to 3) inflorescences per stem.

*Size.*—To 41 cm tall to a terminal inflorescence and 7 mm wide at base.

*Internode length.*—2 cm to 8.5 cm.

*Surface texture.*—Strigose.

*Color.*—Yellow Green 146C mottled Green 137A.

Leaf (basal):

*Type.*—Simple.

*Shape.*—Ovate.

*Arrangement.*—Basal.

*Blade size.*—Grows to 7.5 cm long and 3.5 cm wide.

*Margins.*—Entire to sparsely serrate.

*Apex.*—Acute.

*Base.*—Attenuate.

*Surface texture.*—Strigose on both sides.

*Venation.*—Pinnate.

*Color.*—Topside Green 137A, bottom side Green 137B.

*Petiole description.*—Grows to 9.5 cm long and 2 mm wide, glabrous, Yellow Green 147B with Greyed Purple 187B at base.

Leaf (stem):

*Type.*—Simple.

*Shape.*—Ovate to lanceolate.

*Arrangement.*—Alternate.

*Blade size.*—Grows to 10 cm long and 3.8 cm wide.

*Margins.*—Entire.

*Apex.*—Acuminate.

*Base.*—Attenuate.

*Surface texture.*—Strigose on both sides.

*Venation.*—Pinnate.

*Color.*—Topside Green 137A bottom side Green 137B.

*Petiole description.*—On lowermost leaves only, clasping, grows to 5 cm long and 5 mm wide above the clasp, scabrous, Yellow Green 146B.

Inflorescence:

*Type.*—Composite on terminal stalked heads.

*Number of flowering stems per plant.*—About 50.

*Flowering stem.*—Grows to 41 cm tall from the base of the plant to the terminal inflorescence and can grow to 14 cm long from the top stem leaf to the base of an inflorescence; unbranched to branched, with 1 to 3 inflorescences per stem; diameter growing to 9 mm wide near the inflorescence; strigose; Yellow Green 146C mottled Green 137A.

*Size.*—Grows to 10 cm wide and 5.5 cm deep as disc enlarges.

*Form.*—Ray florets held slightly reflexed, mature disc is conic.

*Immature inflorescence.*—Grows to 2.8 cm wide and 2.5 cm deep, ray florets held upright and rolled up so only the back color shows, Greyed Purple N186D except tips where Yellow Green 145B, disc color Greyed Purple 187A.

*Ray florets.*—Without pistil or stamen, about 20, grow to 44 mm long and 13 mm wide, sometimes cupped down, elliptic to oblanceolate with the tip two-toothed (each acute), entire margins, base attenuate, glabrous on both sides; topside Red Purple 64B maturing to Red Purple 70A; bottom side Greyed Purple 186B.

*Disc.*—Flat becoming conic, becoming 33 mm deep and 39 mm wide with maturity, Greyed Orange 172B to Greyed Purple 187A.

*Disc florets.*—About 400 in number, each with 1 pistil and 4 stamen, grow to 9 mm long and 1.5 mm wide, each with one persistent, very stiff linear bract (12 mm long with the tip Greyed Purple 187A to top 2 mm colored Orange 24A to Green 137B to White NN155A on bottom ¼); corolla 5 mm long and 1.5 mm wide, tubular, 5 lobed, glabrous, Green 138B to lobes Greyed Purple 187A; pistil 10 mm long, ovary 3 mm long, White NN155D, style 4.5 mm long Yellow Green 145D, 2-branched stigma spreading 2 mm wide, Greyed Purple 187A; stamen 7 mm long, filaments 4.5 mm long and White NN155B, anthers 2.5 mm long and Grey Brown 199A, pollen Yellow Orange 16A.

*Phyllaries.*—In 4 leafy series, area grows to 35 mm wide and 12 mm deep, lobes lanceolate in shape, reflexed, grow to 14 mm long and 3 mm wide, Yellow Green 147A, margins strigose, tip acute, strigose on both sides.

*Receptacle.*—Grows to 12 mm wide and 21 mm deep, White NN155B on the inside and Greyed Purple 187A on the outside edge.

*Bloom period.*—July through October in Canby, Oreg.

*Fragrance.*—Strong, sweet, floral.

*Lastingness.*—Each inflorescence lasts about two weeks in Canby, Oreg.

Seeds: 3 mm long and 2.5 mm wide, oval, Brown 200C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

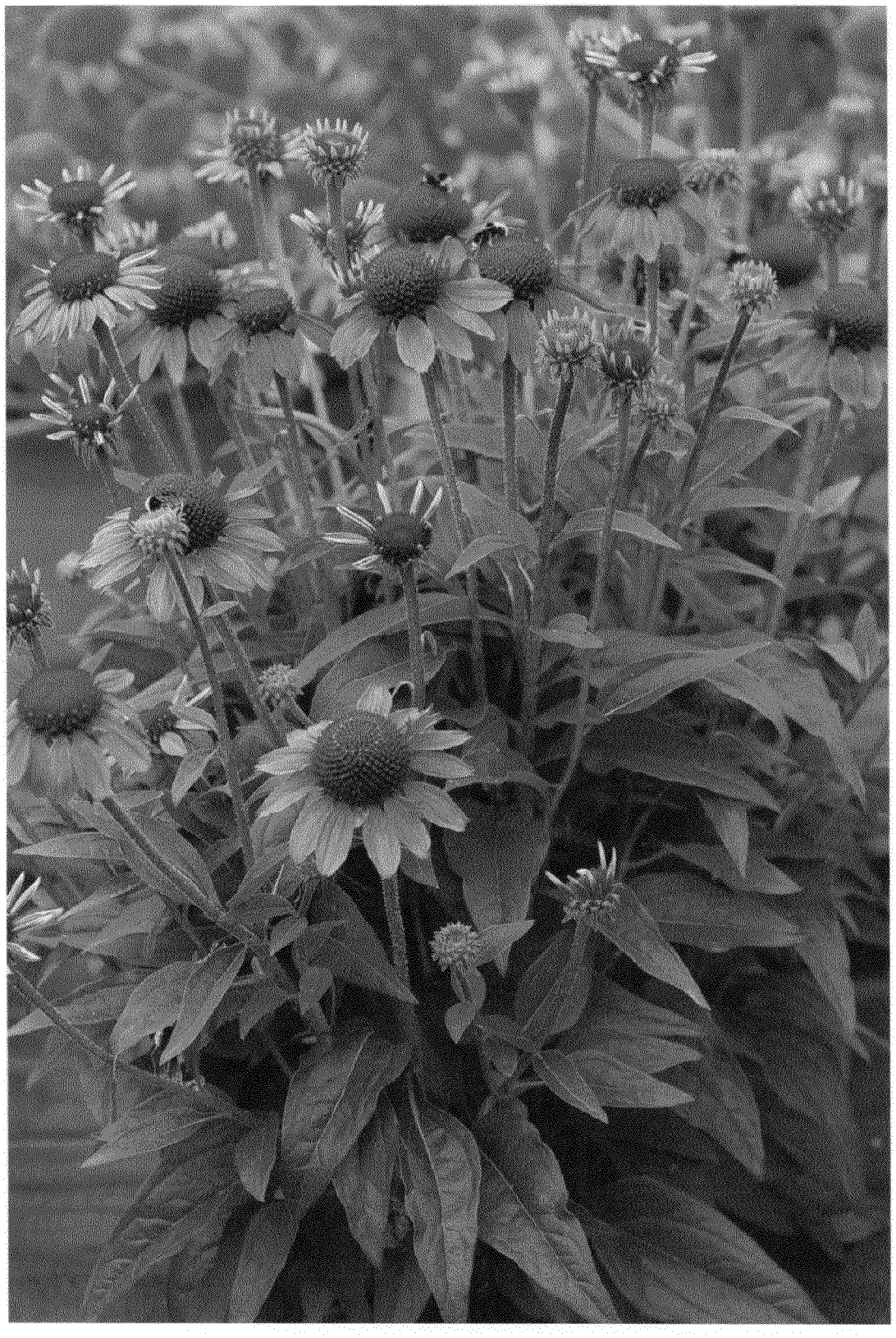

* * * * *